United States Patent [19]

Mertens et al.

[11] Patent Number: 4,925,845

[45] Date of Patent: May 15, 1990

[54] 2 HETEROARYL 3,3 DIALKYL-5-(3 OXO-2,3,4,5 TETRAHYDRO-6 PYRIDAZINYL)-3H-INDOLES

[75] Inventors: Alfred Mertens, Schriesheim; Wolfgang von der Saal, Weinheim; Lothar Kling, Mannheim; Bernd Müller-Beckmann, Grünstadt, all of Fed. Rep. of Germany

[73] Assignee: Boehringer Mannheim GmbH, Mannheim, Fed. Rep. of Germany

[21] Appl. No.: 159,744

[22] Filed: Feb. 24, 1988

[30] Foreign Application Priority Data

Feb. 27, 1987 [DE] Fed. Rep. of Germany ....... 3706427

[51] Int. Cl.$^5$ ..................... A61K 31/50; C07D 401/04
[52] U.S. Cl. .................................. 514/254; 514/183; 514/222.2; 514/226.8; 514/227.8; 514/229.2; 514/231.5; 514/241; 514/242; 514/339; 544/3; 544/53; 544/56; 544/63; 544/66; 544/67; 544/88; 544/98; 544/111; 544/179; 544/180; 544/182; 544/230; 544/238; 546/373; 564/148
[58] Field of Search ...................... 544/238; 514/254

[56] References Cited

U.S. PATENT DOCUMENTS

| 3,845,050 | 10/1974 | Lebkuechner | 544/238 |
|---|---|---|---|
| 4,225,711 | 9/1981 | Steinman | 544/238 |
| 4,258,185 | 3/1981 | Nakao et al. | 544/238 |
| 4,591,591 | 5/1986 | Robertson | 514/254 |
| 4,595,028 | 6/1986 | Campbell | 544/238 |
| 4,617,302 | 10/1986 | Robertson | 514/254 |
| 4,631,279 | 12/1986 | Robertson | 544/238 |
| 4,647,564 | 3/1987 | Robertson | 544/238 |
| 4,695,567 | 9/1987 | Mertens | 544/238 |
| 4,816,454 | 3/1989 | Zoeller | 544/238 |
| 4,835,280 | 5/1989 | Martens | 544/238 |
| 4,847,251 | 7/1989 | Mertens et al. | 514/254 |
| 4,851,406 | 9/1989 | Mertens et al. | 544/238 |
| 4,870,077 | 9/1989 | von der Saal et al. | 514/254 |

FOREIGN PATENT DOCUMENTS

| 0052442 | 5/1982 | European Pat. Off. . | |
| 0122494 | 10/1984 | European Pat. Off. . | |
| 0223937 | 3/1987 | European Pat. Off. | 544/238 |
| 0280224 | 8/1988 | European Pat. Off. | 544/238 |
| 2845220A1 | 4/1980 | Fed. Rep. of Germany . | |
| 2530246 | 1/1984 | France . | |

OTHER PUBLICATIONS

Wentrup, Journal of the American Chemical Society, vol. 106, No. 12, Jun. 13, 1984, pp. 3705–3706, "Synthesis of 1-Azaazulene and Benz[a]azulene by Carbene Rearrangement".

Journal of the Chemical Society (C), 1970, pp. 829–833, "Synthetic Uses of Polyphosphoric Acid and its Ethyl Ester, Part II, Synthesis of Indolin-2(3H)-ones and Imidazoquinolines".

Derwent abstract of Japan 58-8016 1/18/83.

*Primary Examiner*—Donald G. Daus
*Attorney, Agent, or Firm*—Armstrong, Nikaido, Marmelstein, Kubovcik & Murray

[57] ABSTRACT

Gem 3 dialkyl or spiro 4 aryl or heteroaryl 5 heterocyclic 3 H indoles and their pharmaceutically acceptable salts are prepared. They are useful for reducing blood pressure producing a positive inotropic action influencing thrombocyte aggregation and improving microcirculation. Hydrazinophenyl heterocyclic intermeidates are also disclosed.

17 Claims, No Drawings

2 HETEROARYL 3,3 DIALKYL-5-(3 OXO-2,3,4,5 TETRAHYDRO-6 PYRIDAZINYL)-3H-INDOLES

The present invention is concerned with new 3H-indoles, processes for the preparation thereof and pharmaceutical compositions containing them.

The new 3H-indoles according to the present invention are compounds of the general formula:

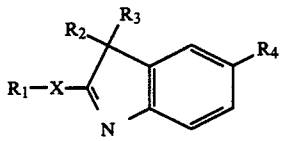

wherein $R_1$ is a phenyl ring of the general formula:

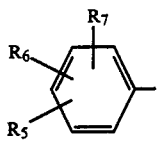

wherein $R_5$, $R_6$ and $R_7$ can be the same or different and each represents a hydrogen atom or an alkanesulphonyloxy, trifluoromethanesulphonyloxy, alkanesulphonylamino, trifluoromethanesulphonylamino, N-alkyl-alkanesulphonylamino, N-alkyl-trifluoromethanesulphonylamino, alkylsulphenylmethyl, alkylsulphinylmethyl or alkylsulphonylmethyl radical, a carbonyl group substituted by hydroxyl, alkoxy, amino, alkylamino or dialkylamino, a sulphonyl group substituted by amino, alkylamino or dialkylamino, whereby a methylene group in the 4-position can be replaced by a sulphur or oxygen atom, an alkylcarbonylamino, aminocarbonylamino or alkylamino carbonylamino radical, an alkylthio, alkylsulphinyl or alkylsulphonyl radical, a nitro, halogen, amino, hydroxyl, alkyl, alkoxy, alkenyloxy, alkynyloxy, cyanoalkoxy, carboxyalkoxy, alkoxycarbonylalkoxy, dialkylamino, 1-imidazolyl, trifluoromethyl or cyano group or $R_1$ is an optionally substituted naphthyl radical or $R_1$ is a saturated or unsaturated heterocyclic five-membered ring containing up to 4 heteroatoms or a saturated or unsaturated six-membered ring containing up to 5 heteroatoms, whereby the heteroatoms can be the same or different and are oxygen, sulphur or nitrogen atoms and, if desired, can carry an oxygen atom on one or more nitrogen atoms and the five- and six-membered. rings are optionally substituted one or more times by alkyl, alkoxy, alkylthio, hydroxyl, nitro, amino, halogen or cyano or can be condensed with a phenyl ring to form a bicyclic radical, or, when X is a valency bond, besides the above-mentioned groups, $R_1$ can also be a hydrogen atom, an alkyl, cycloalkyl, alkenyl, cycloalkenyl, alkynyl, alkoxyalkyl, carboxyalkyl, alkoxycarbonylalkyl, aminoalkyl, hydroxyalkyl, amino, alkylamino, alkylcarbonylamino, formylamino or alkylsulphonylamino radical, $R_2$ is an alkyl, alkenyl, cycloalkyl or optionally substituted phenyl radical, $R_3$ is an alkyl, alkenyl, cycloalkyl or optionally substituted phenyl radical or, together with $R_2$, is a cycloalkylene radical, $R_4$ is a heterocyclic five-membered ring with up to 4 heteroatoms or a heterocyclic six-membered ring with up to 5 heteroatoms, whereby the heteroatoms of the said five- and six-membered rings can be the same or different and are nitrogen, oxygen or sulphur atoms and the said five- and six-membered rings are optionally substituted one or more times by alkyl, alkoxy, alkoxyalkyl, alkylthio, hydroxyl, hydroxyalkyl, amino, halogen, oxo or cyano groups, X is a valency bond, an alkylene or vinylene radical, an imino group —NH— or a carbonylamino group —CONH—, the tautomers thereof and the physiologically acceptable salts thereof with inorganic and organic acids.

When compounds of general formula (I) are prepared which contain a centre of asymmetry, the present invention also includes the optically-active forms and racemic mixtures of these compounds.

The new compounds according to the present invention possess valuable pharmacological properties and, in particular, they increase the power of the heart and/or reduce the blood pressure and/or influence the thrombocyte function and improve the microcirculation.

When, in general formula (I), $R_1$ is a phenyl ring, then the alkyl moieties of the substituents mentioned in the case of $R_5$, $R_6$ and $R_7$ contain up to 5 carbon atoms and preferably up to 4 carbon atoms. Preferred in this sense are, for example, the methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethyl-ethanesulphonylamino, N-isopropyl-ethanesulphonylamino, N-methyl-n-propanesulphonylamino, N-n-propyl-n-propanesulphonylamino, N-methyl-trifluoromethanesulphonylamino, N-ethyl-trifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, trifluoromethyl, methylamiaosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methyl-isopropylaminosulphonyl, acetylamino, propionylamino, methylcarbonylamino, ethylaminocarbonylamino and propylaminocarbonylamino radicals, as well as the methyl, ethyl, propyl, methoxy, ethoxy, propoxy, allyloxy, but-2-enyloxy, but-3-enyloxy, pent-2-enyloxy, propargyloxy, but-2-ynyloxy, but-3-ynyloxy, cyanomethoxy, cyanoethoxy, methoxycarbonylmethoxy, methoxycarbonylethoxy, methylthio, ethylthio, methylsulphinyl, ethylsulphinyl, methylsulphonyl and ethylsulphonyl radicals.

In the case of sulphonyl groups which can be substituted by cyclic imino groups, there are preferred the morpholino-, thiomorpholino-, pyrrolidino-, piperidino- and hexamethyleneiminosulphonyl groups.

For $R_5$, there is especially preferred a hydrogen atom, an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by hydroxyl, alkoxy, amino, alkylamino or dialkylamino or a sulphonyl group substituted by amino, dialkylamino or morpholino group, whereby each of the above-mentioned alkyl moieties can contain 1 or 2 carbon atoms, a nitro or cyano group or an alkylaminosulphonyl radical containing up to 4 carbon atoms, an alkylcarbonylamino, aminocarbonylamino or N-alkylaminocarbonylamino radical, an alkylthio, alkylsulphinyl or alkylsulphonyl radical, whereby each of the abovementioned alkyl moieties can contain 1 or 2 carbon atoms, a halogen atom, an amino or hydroxyl group or a dialkylamino, alkyl, alkoxy, alkenyloxy or alkynyloxy radical preferably containing up to 3 carbon atoms, a cyanomethoxy or methoxycarbonylmethoxy radical, a trifluoromethyl radical or a 1-imidazolyl radical; for $R_6$ there is especially preferred a hydrogen atom, an alkyl radical containing up to 3 carbon atoms, an alkoxy or dialkylamino radical containing 1 or 2 carbon atoms in each alkyl moiety or a halogen atom; and for $R_7$ there is preferred a hydrogen atom or a methoxy radical.

The phenyl moiety can contain up to 3 of the said substituents.

Preferred monosubstituted phenyl compounds are the hydroxy-, $C_1$-$C_3$-alkyl-, $C_1$-$C_3$-alkoxy-, allyloxy-, propargyloxy-, cyanomethoxy-, methoxycarbonylmethoxy-, halo-, nitro-, cyano-, aminocarbonyl-, methoxycarbonyl-, amino-, $C_1$-$C_3$-dialkylamino-, $C_1$-$C_3$-alkylthio-, $C_1$-$C_3$alkylsulphinyl-, $C_1$-$C_3$-alkylsulphonyl-, $C_1$-$C_3$-alkylsulphonyloxy- and the 1-imidazolylphenyls, the substituent being in the 2-, 3- or 4-position.

Preferred disubstituted phenyls contain, as substituents, alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radicals, carbonyl groups substituted by hydroxyl, alkoxy, amino, alkylamino or dialkylamino and sulphonyl groups substituted by amino, dialkylamino or morpholino, alkylaminosulphonyl, alkylcarbonylamino, aminocarbonylamino or N-alkylaminocarbonylamino, hydroxyl, alkyl, alkoxy, allyloxy, propargyloxy, cyanomethoxy, methoxycarbonylmethoxy, cyano, halogen, nitro, amino, dialkylamino, alkylthio, alkylsulphinyl, alkylsulphonyl or 1-imidazolyl, whereby the two substituents can be the same or different and can be in the 2,3-, 2,4-, 2,5-, 2,6-,, 3,4- or 3,5- position but preferably in the 2,4-, 2,5- or 3,4-position and the said alkyl radicals, alone or in combination with other moieties, can contain up to 3 carbon atoms.

A preferred trisubstituted phenyl radical is the 3,4,5-trimethoxyphenyl radical.

When $R_1$ signifies a heterocyclic five-membered ring containing up to 4 hetero atoms or a heterocyclic six-membered ring containing up to 5 hetero atoms, the hetero atoms in the said five- and six-membered rings being the same or different and being nitrogen, oxygen or sulphur atoms and one or more nitrogen atoms optionally carry an oxygen atom, then there is preferred a pyrrole, furan, thiophene, pyrazole, imidazole, thiazole, isothiazole, oxazole, isoxazole, triazole, tetrazole, thiadiazole, oxadiazole, pyrazine, N,N-dioxypyrazine, pyrimidine, N,N-dioxypyrimidine, pyridazine, oxazine, thiazine, triazine, tetrazine, pyridine, N-oxypyridine, piperidine, piperazine, morpholine or thiomorpholine radical.

Alkyl, alkoxy and alkylthio substituents in the heterocyclic five- and six-membered rings can contain up to 6 and preferably up to 4 carbon atoms, the methyl, ethyl, methoxy, ethoxy, methylthio and ethylthio radicals being preferred. Halogen is to be understood to mean fluorine, chlorine or bromine, chlorine being preferred.

When the heterocyclic five- and six-membered rings are condensed with a phenyl ring, then there are preferred the indole, indazole, benzimidazole, quinoline, isoquinoline, cinnoline, phthalazine, quinazoline, quinoxaline, benzofuran, benzothiophene, benzoxazole, benzisoxazole, benzothiazole or benzisothiazole radical, as well as the naphthyl radical.

When X signifies a valency bond and $R_1$ an alkyl, alkenyl or alkynyl radical, then there are to be understood straight-chained and branched radicals containing up to 10 carbon atoms. Preferred in this sense are the methyl, ethyl, propyl, butyl, pentyl, hexyl, vinyl, propenyl and propynyl radicals. When X signifies a valency bond and $R_1$ a cycloalkyl or cycloalkenyl radical, then thereunder are to be understood rings with 3 to 7 members. Preferred in this sense are the cyclopropyl, cyclobutyl, cyclopentyl, cyclohexyl, cyclopentenyl and cyclohexenyl radicals.

When X signifies a valency bond and $R_1$ an alkoxyalkyl, carboxyalkyl, alkoxycarbonylalkyl, hydroxyalkyl, aminoalkyl, alkylamino or alkylcarbonylamino radical, then the alkyl and alkoxy moieties can contain up to 6 carbon atoms. Preferred in this sense are the ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylethyl, aminomethyl, aminoethyl, aminopropyl, aminobutyl, hydroxymethyl, hydroxyethyl, hydroxypropyl, hydroxybutyl, methylamino, ethylamino, propylamino, butylamino, acetylamino, propionylamino and methylsulphonylamino radicals.

By halogen is to be understood fluorine, chlorine and bromine, chlorine being preferred.

When, in general formula (I), $R_2$ and $R_3$ signify alkyl radicals, then there are to be understood thereunder straight-chained and branched alkyl radicals containing up to 6 carbon atoms, the methyl, ethyl, propyl and butyl radicals being preferred.

When $R_2$ and $R_3$, together with the carbon atom to which they are attached, form a carbocyclic ring, then there are to be understood thereunder rings with 3 to 7 members, the cyclopropane, cyclobutane, cyclopentane and cyclohexane rings being preferred.

When $R_4$ signifies a heterocyclic five- or six-membered ring with up to 4 or up to 5 identical or different hetero atoms, respectively, such as oxygen, sulphur or nitrogen atoms, and if these five- and six-membered rings are optionally substituted one or more times by alkyl, alkoxy, alkoxyalkyl, alkylthio, oxo, hydroxyl, hydroxyalkyl, amino, halogen or cyano, then, in this sense, there are preferred the 3-oxo-2,3-dihydro-6-pyridazinyl, 5-alkyl-3-oxo-2,3-dihydro-6-pyridazinyl, 3-oxo-2,3,4,5-tetrahydro-6-pyridazinyl, 3-oxo-2,3-dihydro-6-pyridazinyl, 5-alkyl-3-oxo-2,3,4,5-tetrahydro-6-pyridazinyl, 5-hydroxyalkyl-3-oxo-2,3,4,5-tetrahydro-6-pyridazinyl, 3-cyano-6-alkyl-2-oxo-1,2-dihydro-5-pyridinyl, 6-alkyl-2-oxo-1,2-dihydro-5-pyridinyl, 3-amino-2-oxo-1,2-dihydro-5-pyridinyl, 3-amino-6-alkyl-2-oxo-1,2-dihydro-5-pyridinyl, 3-hydroxy6-alkyl-2-oxo-1,2-dihydro-5-pyridinyl, 3-oxo-2H-3,4-dihydro-1,4-thiazin-6-yl, 6-oxo-1,6-dihydro-1,2,4-triazin-3-yl, 6-oxo-1,4,5,6-tetrahydro-1,2,4-triazin-3-yl, 5-oxo-4,5-dihydro-6H-1,3,4-oxadiazin-2-yl, 5-oxo4,5-dihydro-6H-1,3,4-thiadiazin-2-yl, 3-oxo-2,3-dihydro1,2,4-triazin-6-yl, 3-oxo-2,3,4,5-tetrahydro-1,2,4triazin-6-yl, 2-oxo-2,3-dihydro-6H-1,3,4-oxadiazin-5-yl, 2-oxo-2,3-dihydro-6H-1,3,4-thiadiazin-5-yl, 5-alkyl-3-oxo-2,3,4,5-tetrahydro-1,2,4-triazin-6-yl, 2-oxo-1,2-dihydro-5-pyrimidinyl, 4-alkyl-2-oxo-1,2-dihydro-5-pyrimidinyl, 2-oxo-1,2-dihydro-5-pyrazinyl, 3-alkyl-2-oxo-1,2-dihydro-5-pyrazinyl, 6-alkyl-2-oxo-1,2-dihydro5-pyrazinyl, 4,4-dialkyl-5-oxo-4,5-dihydro-3-pyrazolyl, 2-oxo-4-pyrrolidinyl, 3-alkyl-2-oxo-4-pyrrolidinyl, 5-oxo-4,5-dihydro-1,2,4-triazol-3-yl, 4-alkyl-5-oxo-4,5-dihydro- 1,2,4-triazol-3-yl, 2-oxo-2,-dihydro-4(5)-imidazolyl and 5(4)-alkyl-2-oxo-2,3-dihydro-4(5)-imidazolyl radicals.

When, in general formula (I), X signifies an alkylene radical, then thereunder are to be understood alkylene radicals containing up to 4 carbon atoms, the methylene and ethylene radicals being preferred.

Especially preferred compounds of general formula (I) are those in which $R_1$ is a phenyl radical of general formula (II) in which $R_5$ is a hydrogen atom, a methanesulphonyloxy, trifluoromethanesulphonyloxy, methanesulphonylamino, trifluoromethanesulphonylamino, methylthio, methylsulphinyl, methylsulphonyl, hydroxyl, methyl, methoxy, propargyloxy, trifluoromethyl or 1-imidazolyl radical, $R_6$ is a hydrogen atom or a methyl, methoxy, dimethylamino or chlorine substituent, $R_7$ is a hydrogen atom or a methoxy radical; or $R_1$ is a pyrrole, furan, thiophene, pyrazole, imidazole, isothiazole, thiazole, oxazole, triazole, tetrazole, thiadiazole, isoxazole, oxadiazole, pyridine, N-oxypyridine, pyrazine, N,N-dioxypyrazine, pyrimidine, N,N-dioxypyrimidine, pyridazine, oxazine, thiazine, triazine, tetrazine, piperidine, piperazine, morpholine or thiomorpholine radical, as well as the methyl-, ethyl-, methoxy-, ethoxy-, methylthio-, ethylthio- and chlorinesubstituted derivatives thereof; or an indole, indazole, quinoline or isoquinoline radical or a naphthyl radical; or, when X is a valency bond or an imino group—NH—, besides the above-mentioned groups, $R_1$ also signifies a hydrogen atom or a methyl, ethyl, propyl, butyl, pentyl, hexyl, propenyl, cyclopentyl, cyclohexyl, methylamino, amino, acetamido or formamide radical, $R_2$ and $R_3$ are the same and signify methyl radicals or $R_2$ and $R_3$, together with the carbon atom to which they are attached, form a cyclopentane or cyclohexane ring, $R_4$ is a 3-oxo-2,3,4,5-tetrahydro-6-pyridazinyl, 5-methyl3-oxo-2,3,4,5-tetrahydro-6-pyridazinyl, 5-hydroxymethyl3-oxo-2,3,4,5-tetrahydro-6-pyridazinyl, 3-oxo-2,3-dihydro-6-pyridazinyl, 3-cyano-6-methyl-2-oxo-1,2-dihydro-5-pyridinyl, 3-oxo-2,3,4,5-tetrahydro-1,2,4-triazin-6-yl, 2-oxo-4,5-dihydro-6H-1,3,4-oxadiazin-5-yl, 6-oxo-1,4,5,6-tetrahydro-1,2,4-triazin-3-yl, 5-oxo-4,5-dihydro-6H-1,3,4-oxadiazin-2-yl, 2-oxo-1,2-dihydro-5-pyrimidinyl, 2-oxo-1,2-dihydro-5-pyrazinyl, 4,4-dimethyl-5-oxo-4,5-dihydro-3-pyrazolyl, 2-oxo-4-pyrrolidinyl, 4-methyl-5-oxo-4,5-dihydro-1,2,4-triazol-3-yl or 5(4)-methyl-2-oxo-2,3-dihydro-4(5)-imidazolyl radical and X is a valency bond a vinylene or methylene radical, an imino group or a carbonylamino group.

The compounds of general formula (I) according to the present invention can be prepared according to indole synthesis methods known from the literature, in which regard reference is made to:

(a) P. L. Julian, E. W. Meyer and H. C. Printy, in R. C. Elderfield (ed.), Heterocyclic Compounds, Vol. 1, pp. 1–231, pub. John Wiley and Sons, New York, 1952 (b) R. K. Brown, in W. J. Houlihan (ed.), Heterocyclic Compounds, Vol. 25, Part I, pp. 227–537, pub. John Wiley and Sons, New York, 1972.

The synthesis route illustrated in the following Scheme 1 is especially advantageous:

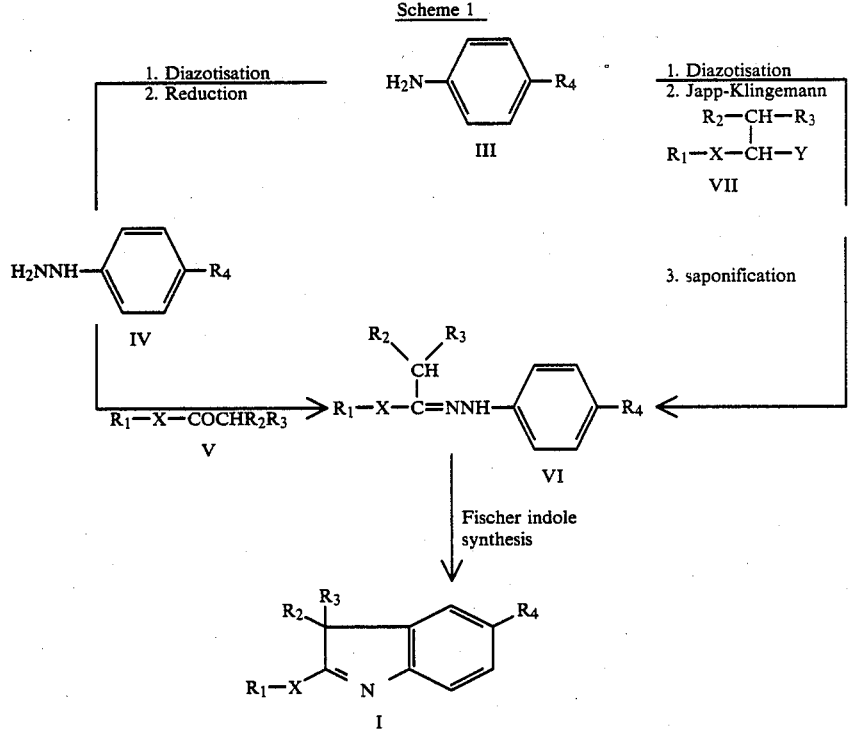

As can be seen from Scheme 1, the compounds of general formula (III), which are known from the literature or are prepared by processes known from the literature, in which $R_4$ has the given meaning, can be diazotised and the diazonium salt reduced to the hydrazine (IV). By reaction of this hydrazine with a compound of the general formula:

$$R_1—X—COCHR_2R_3 \quad (V)$$

in which $R_1$, $R_2$, $R_3$ and X have the above-given meanings, there is obtained the hydrazone (VI) which can be cyclised by a Fischer indole synthesis to give a compound of general formula (I). On the other hand, the hydrazones of general formula (VI) can also be obtained by reacting the diazonium salt of the amine (III) in a Japp-Klingemann reaction with a compound of the general formula:

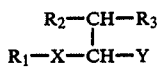

(VII)

in which $R_1$, $R_2$, $R_3$ and X have the above-given meanings and Y is a residue activating the methine radical. This compound can be, for example, an aldehyde, ketone, ester, carboxylic acid or nitrile. The azo compound formed as an intermediate in the reaction mixture can, without isolation, be directly saponified to the hydrazone.

The compounds of general formula (VI) are new and also the subject of the present invention.

The diazotisation of the amine (III) is preferably carried out under neutral or acidic conditions in a polar solvent, such as water, methanol, ethanol, glacial acetic acid, hydrochloric acid, sulphuric acid or phosphoric acid, at a temperature of from $-70°$ to $+50°$ C. but preferably of from $-5°$ to $+10°$ C.

For the diazotisation, there are preferably used salts or organic esters of nitrous acid, for example sodium nitrite, potassium nitrite or amyl nitrite.

The reduction of the diazonium salt is preferably carried out in the above-mentioned solvents in which the diazotisation is carried out at a temperature of from $-50°$ C. to the boiling point of the solvent but preferably at a temperature of from $0°$ to $80°$ C. As reducing agents, there can be used alkali metal sulphites, sulphur dioxide, dithionites, stannous chloride, zinc dust, iron, sodium amalgam, triphenylphosphine or endiols, as well as electrochemical reduction.

The reaction of the hydrazines with compounds of general formula (V) can be carried out in solvents, for example water, alcohols, benzene, toluene, dioxan, dimethylformamide, diethyl ether or tetrahydrofuran, at a temperature of from $-80°$ C. to the boiling point of the solvent used. The addition of an inorganic or organic acid, for example hydrochloric acid, sulphuric acid, phosphoric acid or acetic acid, is also advantageous.

The Japp-Klingemann reaction is advantageously carried out in the solvents in which the above-described diazotisation can be carried out. Thus, these are, in particular, water, methanol, ethanol, glacial acetic acid, hydrochloric acid, sulphuric acid or phosphoric acid. The reaction is carried out at a temperature of from $-50°$ to $+80°$ C. but preferably of from $0°$ to $25°$ C. The subsequent saponification can be carried out thermally or after the addition of a base or acid, for example aqueous sodium hydroxide solution, aqueous potassium hydroxide solution, hydrochloric acid, sulphuric acid, phosphoric acid or glacial acetic acid, at a temperature of up to the boiling point of the solvent.

The Fischer indole synthesis of the hydrazones (VI) is carried out thermally without a solvent or in a solvent, such as an alcohol, nitrobenzene, acetic acid, xylene, cumol or toluene, or in the presence of an acidic catalyst which can, however, also be a solvent, in which case hydrochloric acid, sulphuric acid, phosphoric acid, polyphosphoric acid, glacial acetic acid, formic acid, stannous chloride, boron trifluoride, a cation exchanger, sulphosalicylic acid or a polyphosphate ester can be used, the temperature being from $0°$ C. to the boiling point of the solvent used.

The hydrazones of general formula (VI) can possibly also be prepared from the amines (III) via the sydnones (X) according to the following Scheme 2:

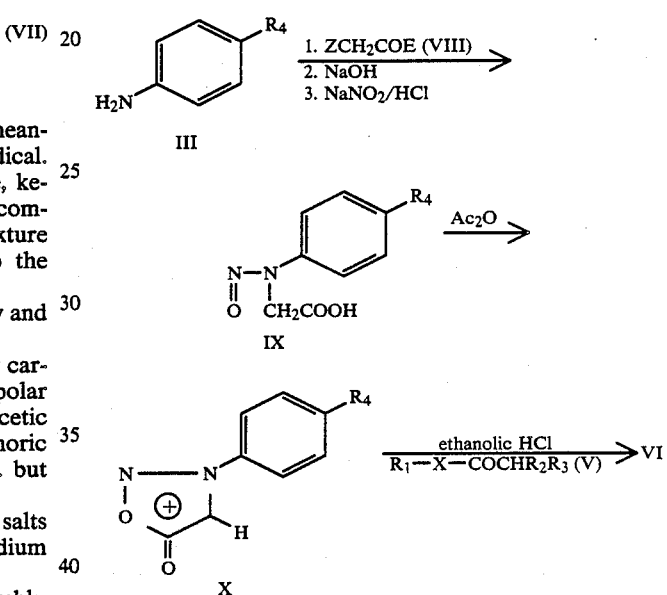

The reaction of amines (III) with haloacetic acid esters (VIII), in which Z is a halogen atom, such as fluorine, chlorine, bromine or iodine but preferably bromine, is advantageously carried out in a polar or non-polar solvent, for example methylene chloride, toluene, dioxan, an alcohol or dimethylformamide, at a temperature of from $-50°$ C. to the boiling point of the solvent but preferably of from $25°$ to $100°$ C.

The esters thus obtained can be saponified by well-known processes, for example with inorganic bases, such as sodium hydroxide, potassium hydroxide, sodium hydrogen carbonate or potassium hydrogen carbonate, in protic solvents, such as water or an alcohol, or with inorganic or organic acids, such as hydrochloric acid, sulphuric acid, glacial acetic acid, phosphoric acid or polyphosphoric acid, optionally with the addition of a solvent, such as water or an alcohol.

The nitrosation of the acids obtained to give compounds of general formula (IX) is preferably carried out under neutral or acidic conditions in a polar solvent, such as water, methanol, ethanol, glacial acetic acid, hydrochloric acid, sulphuric acid or phosphoric acid, at a temperature of from $-70°$ to $+50°$ C. but preferably of from $-5°$ to $+10°$ C. For the nitrosation, there are preferably used inorganic salts or organic esters of nitrous acid, for example sodium nitrite, potassium nitrite or amyl nitrite.

The reaction of the N-nitrosocarboxylic acids (IX) to give the sydnones (X) takes place in an inert solvent, for example dioxan, diethyl ether, tetrahydrofuran or toluene, with water-removing agents, for example acetic anhydride, propionic acid anhydride, sulphuric acid, phosphorus pentoxide, phosphorus pentachloride or phosphorus trichloride, at a temperature of from −50° C. to the boiling point of the solvent but preferably of from 25° to 100° C.

The sydnones (X) can be decomposed under acidic conditions to the hydrazones (IV) which are taken up in situ with the ketones (V) to give the hydrazones (VI). As acids for the saponification of the sydnones, there can be used inorganic acids, such as hydrochloric acid, sulphuric acid, phosphoric acid or polyphosphoric acid, or organic acids, such as glacial acetic acid, at a temperature of from −70° to +100° C. but preferably of from 0° to 70° C.

When $R_4$ in compounds of general formula (I) is a 3-oxo-2,3,4,5-tetrahydro-6-pyridazinyl or 5-methyl-3-oxo-2,3,4,5-tetrahydro-6-pyridazinyl radical, then these compounds of general formula (I) can also be prepared by reacting compounds of the general formula:

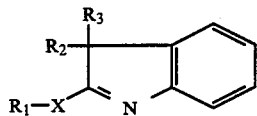

(XI)

in which $R_1$, $R_2$, $R_3$ and X have the above-given meanings, with acid chlorides of the general formula:

$$R_8OOCCH_2-CHR_9COCl \quad (XII)$$

or with carboxylic acid anhydrides of the general formula:

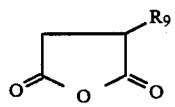

(XIII)

in which $R_8$ is an alkyl radical containing up to 6 carbon atoms and $R_9$ is a hydrogen atom or a methyl radical, to give compounds of the general formula:

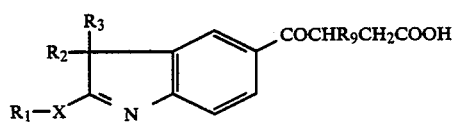

(XIV)

in which $R_1$, $R_2$, $R_3$, $R_9$ and X have the above-given meanings, or the $R_8$ esters thereof.

The compounds of general formula (XIV) can be cyclised with hydrazines to give compounds of general formula (I), in which $R_1$, $R_2$, $R_3$ and X have the above-given meanings and $R_4$ is a 3-oxo-2,3,4,5-tetrahydro-6-pyridazinyl or 5-methyl-3-oxo-2,3,4,5-tetrahydro-6-pyridazinyl radical.

The reaction of compounds of general formula (XI) with compounds of the general formula (XII) or (XIII) is carried out in a solvent, for example carbon disulphide, methylene chloride, dichloroethane or nitrobenzene, in the presence of an excess of a Lewis acid, such as aluminium chloride or aluminium bromide, at a temperature of from 0° to 150° C. but preferably at the boiling point of the solvent or in the presence of a large excess (up to 10 mole) of aluminium chloride in dimethylformamide at a temperature of from 0° to 150° C.

The cyclisation of compounds of general formula (XIV) preferably takes place in a solvent, such as ethanol or isopropanol, or in a solvent mixture, such as isopropanol/water, in the presence of 1 to 5 mole and preferably of 1 to 2 moles of hydrazine hydrate at a temperature of from ambient temperature to the boiling point of the solvent or solvent mixture.

Compounds of general formula (I) can also be subsequently converted into other compounds of general formula (I). This applies, for example. to the following:
(a) For the oxidation of a five- or six-membered ring containing one or more nitrogen atoms to give the corresponding N-oxide. The oxidation is preferably carried out with one or more equivalents of the oxidation agent used, for example with hydrogen peroxide in glacial acetic acid, trifluoroacetic acid or in formic acid at 20° to 100° C. or in acetone at 0° to 60° C., with a per acid, such as performic acid or m-chloroperbenzoic acid, in glacial acetic acid, trifluoroacetic acid, methylene chloride or chloroform, at a temperature of from 0° to 60° C.

(b) For the preparation of compounds of general formula (I), in which $R_1$ is a radical of general formula (II) and $R_5$ is an alkylsulphinyl, alkylsulphonyl, alkylsulphinylmethyl or alkylsulphonylmethyl radical, by subsequent oxidation to a compound of the general formula:

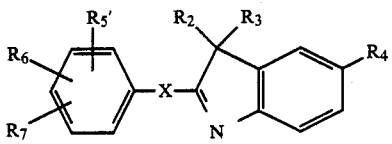

(XV)

in which $R_2$, $R_3$, $R_4$, $R_6$, $R_7$ and X have the same meanings as above and $R_5$ is an alkylthio or alkylsulphenylmethyl radical, in each case with up to 3 carbon atoms in the alkyl moiety. The oxidation is preferably carried out in a solvent or solvent mixture, for example water, water/pyridine, acetone, glacial acetic acid, dilute sulphuric acid or trifluoroacetic acid, depending upon the oxidation agent used, preferably at a temperature of from −80° to 100° C.

For the preparation of an alkylsulphinyl or alkylsulphinylmethyl compound of general formula (I), the oxidation is preferably carried out with one equivalent of the oxidation agent used, for example with hydrogen peroxide in glacial acetic acid, trifluoroacetic acid or formic acid at 0° to 20° C. or in acetone at 0° to 60° C., with a per acid, such as performic acid, in glacial acetic acid or trifluoroacetic acid, at 0° to 50° C. or with m-chloroperbenzoic acid in methylene chloride or chloroform at −20° to +60° C., with sodium metaperiodate in aqueous methanol or ethanol at −15° to +25° C., with bromine in glacial acetic acid or aqueous acetic acid, with N-bromide-succinimide in ethanol, with tert.-butyl hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. or with sulphuryl chloride in methylene chloride at −70° C., the thioether-chlorine complex thereby obtained being preferably hydrolysed with aqueous ethanol.

For the preparation of an alkylsulphonyl or alkylsulphonylmethyl compound of general formula (I), the oxidation is preferably carried out with one or with two or more equivalents, respectively, of the oxidation agent used, for example hydrogen peroxide in glacial acetic acid, trifluoroacetic acid or in formic acid at 20° to 100° C. or in acetone at 0° to 60° C., with a per acid, such as performic acid or m-chloroperbenzoic acid, in glacial acetic acid, trifluoroacetic acid, methylene chloride or chloroform at a temperature of from 0° to 60° C., with nitric acid in glacial acetic acid at 0° to 20° C. or with chromic acid or potassium permanganate in glacial acetic acid, water/sulphuric acid or acetone at 0° to 20° C.

(c) For the preparation of compounds of general formula (I), in which $R_1$ is a radical of general formula (II) and $R_5$ is an alkanesulphonyloxy, trifluoromethanesulphonyloxy, alkanesulphonylamino, N-alkylalkanesulphonylamino, trifluoromethanesulphonyl or N-alkyltrifluoromethanesulphonylamino radical, by the subsequent reaction of a compound of the general formula:

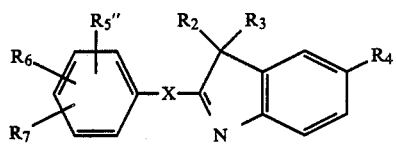

in which $R_2$, $R_3$, $R_4$, $R_6$, $R_7$ and X meanings and $R_5''$ is a hydroxyl or amino group or an N-alkylamino radical, with a sulphonic acid of the general formula:

in which $R_{10}$ is an alkyl radical containing up to 3 carbon atoms or a trifluoromethyl radical, in the presence of a water-removing agent and/or of an agent activating the acid or the amine or with a reactive derivative thereof.

The reaction is preferably carried out in a solvent or solvent mixture, such as methylene chloride, diethyl ether, tetrahydrofuran, dioxan or benzene, optionally in the presence of an acid-binding agent, such as sodium carbonate, triethylamine or pyridine, whereby the latter two can simultaneously also be used as solvent, in the presence of an agent activating the acid or removing water, such as thionyl chloride or phosphorus pentachloride, but preferably with a reactive derivative of a compound of general formula (XVII), for example with an anhydride or halide, such as methanesulphonic acid chloride or ethanesulphonic acid chloride, preferably at a temperature of from 0° to 100° C., for example at a temperature of from ambient temperature to 50° C.

(d) For the preparation of compounds of general formula (I), in which $R_1$ is a radical of general formula (II) and $R_5$ is a carbonyl or sulphonyl group substituted by amino, alkylamino or dialkylamino, by the subsequent reaction of a compound of the general formula:

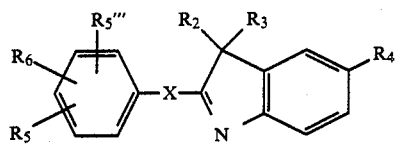

in which $R_2$, $R_3$, $R_4$, $R_6$, $R_7$ and X have the above-given meanings and $R_5'''$ is a carboxyl or hydroxysulphonyl group, or of a reactive derivative thereof, for example an ester or acid chloride, with an amine of the general formula:

in which $R_{11}$ and $R_{12}$ can be the same or different and signify hydrogen atoms or alkyl radicals containing up to 5 carbon atoms, or with a reactive derivative thereof if $R_5'''$ is a carboxyl or hydroxysulphonyl group. The reaction is preferably carried out in a solvent, such as methylene chloride, ethanol, chloroform, carbon tetrachloride, diethyl ether, tetrahydrofuran, dioxan, benzene, toluene, acetonitrile or dimethylformamide, optionally in the presence of an agent activating the acid or of a water-removing agent, for example in the presence of ethyl chloroformate, thionyl chloride, phosphorus trichloride, phosphorus pentoxide, N,N-dicyclohexylcarbodiimide/N-hydroxysuccinimide, N,N-carbonyldiimidazole or N,N-thionyldiimidazole or triphenylphosphine/carbon tetrachloride, or of an agent activating the amino group, for example phosphorus trichloride, and optionally in the presence of an inorganic base, such as sodium carbonate, or of a tertiary organic base, such as triethylamine or pyridine, which can simultaneously serve as solvent, at a temperature of from −25 to +250° C. but preferably at a temperature of from −10° C. to the boiling temperature of the solvent used. Furthermore, water formed during the reaction can be separated off by azeotropic distillation, for example by heating with toluene on a water separator, or by the addition of a drying agent, such as anhydrous magnesium sulphate or a molecular sieve.

However, the reaction is carried out especially advantageously with a corresponding halide, for example the carboxylic acid or sulphonic acid chloride, and a corresponding amine, in which case this can simultaneously serve as solvent, and at a temperature of from 0° to 50° C.

(e) For the preparation of compounds of general formula (I), in which $R_1$ is a phenyl ring of general formula (II) or a heterocyclic five- or six-membered ring and X is a carbonylamino group, by subsequent acylation of compounds of general formula (I), in which $R_2$, $R_3$ and $R_4$ have the given meanings, $R_1$ is a hydrogen atom and X is an NH group. This reaction is preferably carried out by reaction with a carboxylic acid derivative, such as an acid halide, carboxylic acid ester or other activated carboxylic acid derivative, for example an anhydride.

(f) For the preparation of compounds of general formula (I), in which $R_1$ is a radical of general formula (II), $R_5$ being a carboxyl, alkoxycarbonyl, aminocarbonyl, alkoxycarbonylalkoxy or carboxyalkoxy radical, by subsequent alcoholysis and/or hydrolysis of compounds of general formula (I), in which $R_1$ is a radical of general formula (II), $R_5$ being a cyano or cyanoalkoxy radical.

The subsequent alcoholysis and/or hydrolysis is preferably carried out either in the presence of an acid, such as hydrochloric acid, sulphuric acid, phosphoric acid or trichloroacetic acid, or in the presence of a base, such as sodium hydroxide or potassium hydroxide, in an appropriate solvent, such as water, water/methanol, ethanol, water/ethanol, water/isopropanol or water/dioxan, at a temperature of from −10° to 120° C., for example at a temperature between ambient temperature and the boiling temperature of the reaction mixture.

Furthermore, the compounds thus obtained of general formula (I) can subsequently, if desired, be converted into their physiologically acceptable acid-addition salts with inorganic and organic acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned hereinbefore, the new compounds of general formula (I), their tautomers and their physiologically acceptable acid-addition salts display, in the case of a prolonged period of activity, superior pharmacological properties, especially a blood pressure-lowering and/or positive inotropic action and/or influence the thrombocyte function and improve the micro-circulation.

The inotropic activity of certain compounds of the present invention was determined according to the procedure described below.

Male Sprague-Dawley rats weighing between 350 and 450 g were narcotized by intraperitoneal injection of a barbiturate and fitted with instrumentation for the examinations as follows:

A pressure measuring catheter (Miller Mikrotip/-diameter 0.5 mm) was inserted through the arteria carotis dextra into the left ventricle. The pressure inside the left ventricle was continually registered through this catheter. The signal from this Mikrotip was electronically differentiated and $(dp/dt)_{60}$—the slope of the pressure-time curve at a pressure of 60 mmHg - was taken as a measure for the inotropy.

A polypropylene catheter was bound in a vena jugularis for the intravenous in3ection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on an electronically heated and thermostatically controlled operating table.

The test substances were always introduced by intravenous injection, with an injection volume, per injection, of 1 ml/kg body weight. In intervals of 10 min each, doses increasing from 0.01 to 30 mg of the test substances were intravenously injected. In this way dose effect curves for the measured parameters for the investigated substances were obtained.

From the measured data, using a regression calculation, equipotent doses for the positively inotropic effect $(dp/dt)_{60}$ were calculated. In addition, as criterion for the effectiveness of the substances, the maximum effect obtained (maximal increase of $(dp/dt)_{60}$) and its corresponding dose were determined. The table that follows reports the equipotent doses ($DE_{1.5}$ = the dose in mg/kg that leads to an increase of $(dp/dt)_{60}$ of 1.5 mHg/sec) and the maximal effectiveness ($W_{max}$ = the maximal increase of $(dp/dt)_{60}$) and the dose producing the maximum effectiveness.

TABLE

| compound of example | $DE_{1.5}$ mHg/sec [mg/kg i. v.] | $W_{max}$ [mHg/sec] | $W_{max}$ [mg/kg] |
|---|---|---|---|
| 1 | 0.18 | 3.50 | 3.0 |
| 2a | — | 1.10 | 0.10 |
| 3 | — | 2.8 | 3.0 |
| 5a | — | 0.3 | 0.01 |

For the preparation of pharmaceutical compositions, the compounds according to the present invention are mixed in known manner with appropriate pharmaceutical carrier substances, aroma, flavouring and colouring materials and formed, for example, into tablets or dragees or, with the addition of appropriate adjuvants, suspended or dissolved in water or in an oil, for example olive oil.

The new compounds of general formula (I) according to the present invention and the salts thereof can be administered enterally or parenterally in liquid or solid form. As injection medium, it is preferred to use water which contains the additives usual in the case of injection solutions, such as stabilising agents, solubilising agents and/or buffers.

Additives of this kind include, for example, tartrate and citrate buffers, ethanol, complex formers (such as ethylenediamine-tetraacetic acid and the nontoxic salts thereof) and high molecular weight polymers (such as liquid polyethylene oxide). Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the present invention are usually administered in amounts of from 1 to 500 mg. per day, referred to a body weight of 75 kg. It is preferred to administer 2 to 3 times a day 1 or 2 tablets with an active material content of 0.5 to 200 mg. The tablets can also be retarded, in which case only 1 or 2 tablets with 1 to 500 mg. active material have to be given once per day. The active material can also be given by injection 1 to 8 times a day or by continuous infusion, in which case amounts of from 0.5 to 200 mg. per day normally suffice.

Preferred according to the present invention, apart from the compounds described in the Examples, are the following compounds and the tautomers thereof:

2-(3-pyridyl)-3,3-dimethyl-5-(3-oxo-2,3,4,5-tetrahydro-6-pyridazinyl)-3H-indole 2-(4-pyridazinyl)-3,3-dimethyl-5-(3-oxo-2,3,4,5-tetrahydro-6-pyridazinyl)-3H-indole 2-(2-pyrazinyl)-3,3-dimethyl-5-(3-oxo-2,3,4,5-tetrahydro-6-pyridazinyl)-3H-indole 2-(3-thienyl)-3,3-dimethyl-5-(3-oxo-2,3,4,5-tetrahydro-6-pyridazinyl)-3H-indole 2-(4-(thiazolyl)-3,3-dimethyl-5-(3-oxo-2,3,4,5-tetrahydro-6-pyridaz nyl)-3H-indole 2-(2-chlorophenyl)-3,3-dimethyl-5-(3-oxo-2,3,4,5-tetrahydro-6-pyridazinyl)-3H-indole 2-(3-trifluoromethylphenyl)-3,3-dimethyl-5-(3-oxo-2,3,4,5-tetrahydro-6-pyridazinyl)-3H-indole 2-(2-hydroxyphenyl)-3,3-dimethyl-5-(3-oxo-2,3,4,5-tetrahydro-6-pyridazinyl)-3H-indole 2-(4-aminocarbonylphenyl)-3,3-dimethyl-5-(3-oxo-2,3,4,5-tetrahydro-6-pyridazinyl)-3H-indole 2-[4-(1H-imidazol-1-yl)-phenyl]-3,3-dimethyl-5-(3-oxo-2,3,4,5-tetrahydro-6-pyridazinyl)-3H-indole 2-(4-pyridylcarbonylamino)-3,3-dimethyl-5-(3-oxo-2,3,4,5-tetrahydro-6-pyridazinyl)-3H-indole 3,3-dimethyl-5-(3-oxo-2,3,4,5-tetrahydro-6-pyridazinyl)-3H-indole 2-(4-pyridyl)-3,3-dimethyl-5-(3-oxo-2,3,4,5-tetrahydro-1,2,4-triazin-6-yl)-3H-indole 2-(4-pyridyl)-3,3-dimethyl-5-(2-oxo-2,3-dihydro-6H-1,3,4-oxadiazin-5-yl)-3H-indole 2-(4-pyridyl)-3,3-dimethyl-5-(5-oxo-4,5-dihydro-6H-1,3,4-oxadiazin-2-yl)-3H-indole 2-(4-pyridyl)-3,3-dimethyl-5-(2-oxo-1,2-dihydro-5-pyrazinyl)-3H-indole 2-(4-pyridyl)-3,3-dimethyl-5-(4,4-dimethyl-5-oxo-4,5-dihydro-3-pyrazolyl)-3H-indole 2-(4-pyridyl)-3,3-dimethyl-5-(4-methyl-5-oxo-4,5-dihydro-1,2,4-triazol-3-yl)-3H-indole 2-(4-pyridyl)-3,3-dimethyl-5-(3-oxo-2,3-dihydro-6-pyridazinyl)-3H-indole 2-(4-pyridyl)-3,3-dimethyl-5-(5-methyl-3-oxo-2,3-dihydro-6-pyridazinyl)-3H-indole 2-(4-pyridyl)-3,3-diethyl-5-(5-methyl-3-oxo-2,3,4,5-tetrahydro-6-pyridazinyl)-3H-indole 2-(4-pyridyl)-3-methyl-3-ethyl-5-(5-methyl-3-oxo-2,3,4,5-tetrahydro-6-pyridazinyl)-3H-indole 2-(4-pyridyl)-3-methyl-3-butyl-5-(5-methyl-3-oxo-2,3,4,5-tetrahydro-6-pyridazinyl)-3H-indole 2-(4-pyridyl)-3-methyl-3-phenyl-5-(5-methyl-3-oxo-2,3,4,5-tetrahydro-6-pyridazinyl)-3H-indole 2-(4-pyridyl)-3,3-diphenyl-5-(5-methyl-3-oxo-2,3,4,5-tetrahydro-6-pyridazinyl)-3H-indole 2-(4-pyridyl)-spiro[cyclopentan-1,3]-5-[(5-methyl-3-oxo-2,3,4,5-tetrahydro-6-pyridazinyl)-3H-indole]

2-(4-pyridyl)-spiro[cyclohexan-1,3]-5-[(5-methyl-3-oxo-2,3,4,5-tetrahydro-6-pyridazinyl)-3H-indole]

2-(4-pyridyl)-spiro[cyclopropan-1,3]-5-[(5-methyl-3-oxo-2,3,4,5-tetrahydro-6-pyridazinyl)-3H-indole]

2-(4-methoxyphenyl)-spiro[cyclopentan-1,3]-5-[(5-methyl-3-oxo-2,3,4,5-tetrahydro-6-pyridazinyl)-3H-indole]

2-(4-morpholino)-spiro[cyclopentan-1,3]-5-[(5-methyl-3-oxo-2,3,4,5-tetrahydro-6-pyridazinyl)-3H-indole]

The following Examples are given for the purpose of illustrating the present invention:

EXAMPLE 1

2,3,3-Trimethyl-5-(3-oxo-2,3,4,5-tetrahydro-6-pyridazinyl)-3H-indole hydrochloride (a) 6.0 g. (24.9 mMole) 6-(4-hydrazinophenyl)-2,3,4,5-tetrahydropyridazin-3-one hydrochloride in 170 ml. 50% ethanol were mixed at ambient temperature with 3.2 ml. (29.7 mMole) isopropyl methyl ketone. After 3 hours, the reaction mixture was filtered with suction, the residue was washed with 50% ethanol, again suspended in water, neutralised with 2N aqueous ammonia solution and filtered off with suction. There were obtained 5.1 g. isopropyl methyl ketone [4-(3-oxo-2,3,4,5-tetrahydro-6-pyridazinyl)-phenyl hydrazone]; m.p. 98°-100° C.

(b) 3.5 g. (12.9 mMole) of the hydrazone were stirred under an atmosphere of nitrogen in 40 ml. polyphosphoric acid for 3 hours at 120° C. While still warm, the reaction mixture was poured on to ice water, neutralised, extracted with dichloromethane, dried and evaporated. After purification over silica gel (elution agent: dichloromethane/ethanol; 99:1 v/v), the residue was dissolved in ethanol, acidified with ethanolic hydrochloric acid and the crystals formed filtered off with suction. There were obtained 1.9 g. of the title compound in the form of its hydrochloride; m.p. 276° C.

EXAMPLE 2

The following compounds were obtained analogously to Example 1 b), working in glacial acetic acid at 100° C.:

| | designation | yield % | m.p. °C. (solvent) |
|---|---|---|---|
| (a) | 2-(4-pyridyl)-3,3-dimethyl-5-(5-methyl-3-oxo-2,3,4,5-tetrahydro-6-pyridazinyl)-3H-indole from 4-pyridyl-isopropyl ketone-[4-(5-methyl-3-oxo-2,3,4,5-tetrahydro-6-pyridazinyl)-phenylhydrazone]; m.p. 225–227° C. | 63 | 303–305 (methanol) |
| (b) | 2-(4-pyridyl)-3,3-dimethyl-5-(3-oxo-2,3,4,5-tetrahydro-6-pyridazinyl)-3H-indole from 4-pyridyl-isopropyl ketone-[4-(3-oxo-2,3,4,5-tetrahydro-6-pyridazinyl)-phenylhydrazone]; m.p. 247–249° C. | 73 | 269–270 (ethanol) |

EXAMPLE 3

2-Methylamino-3,3-dimethyl-5-(3-oxo-2,3,4,5-tetrahydro-6-pyridazinyl)-3H-indole (a) 5.2 g. (29.7 mMole) 2-Methylamino-3,3-dimethyl-3H-indole were placed in 100 ml. dichloromethane. 16 g. aluminium chloride were introduced and, while cooling with ice, 5.4 g. (33 mMole) succinic acid ethyl ester chloride added dropwise thereto. The reaction mixture was stirred for 4 hours at 25° C., poured on to ice, extracted, dried and evaporated. There were obtained 8.1 g. ethyl 4-oxo-4-(2-methylamino-3,3-dimethyl-3H-indol-5-yl)-butyrate; m.p. 90°–96° C.

(b) 8 g. (26.5 g.) of the above ester were stirred for 2 days at ambient temperature with 4 ml. hydrazine hydrate, 40 ml. ethanol and 0.2 ml. glacial acetic acid, subsequently filtered with suction, the residue purified on silica gel (elution agent: dichloromethane/ methanol saturated with ammonia; 15:1 v/v) and recrystallised from ethanol/water. There were obtained 4.2 g. of the title compound; m.p. 320°–324° C.

EXAMPLE 4

‑2-Phenyl-3,3-dimethyl-5-(3-oxo-2,3,4,5-tetrahydro-6-pyridazinyl)-3H-indole 3 g. (12.5 mMole) 6-(4-hydrazinophenyl)-2,3,4,5-tetrahydropyridazin-3-one hydrochloride, 2.4 g. (16.2 mMole) α-methylpropiophenone and 40 ml. glacial acetic acid were stirred for 8 hours at 100° C. under an atmosphere of nitrogen. The glacial acetic acid was subsequently distilled off and the residue suspended in water, neutralised and filtered with suction. After recrystallisation from ethanol, there was obtained 1.6 g. (40% of theory) of the title compound; m.p. 200°–201° C.

EXAMPLE 5

The following compounds were obtained in the manner described in Example 4:

| designation | yield % | m.p. °C. (solvent) |
|---|---|---|
| (a) 2-(4-methoxyphenyl)-3,3-dimethyl-5-(3-oxo-2,3,4,5-tetrahydro-6-pyridazinyl)-3H-indole | 59 | 264–265 (ethanol) |
| (b) 2-(4-chlorophenyl)-3,3-dimethyl-5-(3-oxo-2,3,4,5-tetrahydro-6-pyridazinyl)-3H-indole | 52 | 250–253 (ethanol) |
| (c) 2-(4-methylphenyl)-3,3-dimethyl-5-(3-oxo-2,3,4,5-tetrahydro-6-pyridazinyl)-3H-indole | 62 | 258–260 (ethanol) |
| (d) 2-(4-methylthiophenyl)-3,3-dimethyl-5-(3-oxo-2,3,4,5-tetrahydro-6-pyridazinyl)-3H-indole | 48 | 226–227 (ethanol) |
| (e) 2-(2-thienyl)-3,3-dimethyl-5-(3-oxo-2,3,4,5-tetrahydro-6-pyridazinyl)-3H-indole | 35 | 216–217 (ethanol) |
| (f) 2'-phenyl-spiro[cyclopentan-1,3']-5'-[(3-oxo-2,3,4,5-tetrahydro-6-pyridazinyl)-3'H-indole] | 41 | 232–233 (methanol) |

EXAMPLE 6

2-(4-Pyridyl)-3,3-dimethyl-5-(3-oxo-2,3-dihydro-6-pyridazinyl)-3H-indole 1.75 g. (5.5 mMole) 2-(4-pyridyl)-3,3-dimethyl-5-(3-oxo-2,3,4,5-tetrahydro-6-pyridazinyl)-3H-indole (see Example 2 b)) was stirred with 25 g. manganese dioxide in 260 ml. dioxan for 20 hours at 90° C. The reaction mixture was subsequently filtered off with suction, the residue stirred up with methanol/methylene chloride and the combined filtrates evaporated to dryness. After crystallisation from methanol, there was obtained 1 g. (58% of theory) of the title compound; m.p. 305°–307° C.

We claim:

1. Compound of the formula

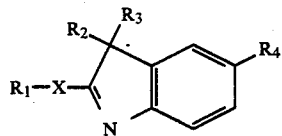

(I)

wherein $R_1$ is a phenyl ring of the formula

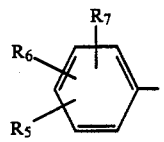

(II)

wherein $R_5$, $R_6$ and $R_7$, which can be the same or different, each represents a hydrogen atom or a $C_1$–$C_5$ alkanesulphonyloxy, trifluoromethanesulphonyloxy, $C_1$–$C_5$ alkanesulphonylamino, trifluoromethanesulphonylamino, N-$C_1$–$C_5$-alkyl-$C_1$–$C_5$ alkanesulphonylamino, N-$C_1$–$C_5$ alkyltrifluoromethanesulphonylamino, $C_1$–$C_5$ alkyl-sulphenylmethyl, $C_1$–$C_5$ alkylsulphinylmethyl or $C_1$–$C_5$-alkylsulphonyl-methyl radical, carbonyl group substituted by hydroxyl, $C_1$–$C_5$ alkoxy, amino, $C_1$–$C_5$ alkylamino or di($C_1$–$C_5$) alkylamino, a sulphonyl group substituted by amino, $C_1$–$C_5$-alkylamino or di($C_1$–$C_5$) alkylamino, a $C_1$–$C_5$ alkylcarbonyl-amino, aminocarbonylamino or $C_1$–$C_5$-alkylaminocarbonylamino radical, a $C_1$–$C_5$ alkylthio, $C_1$–$C_5$-alkylsulphinyl or $C_1$–$C_5$ alkylsulphonyl radical, a nitro, halogen, amino, hydroxyl, $C_1$–$C_5$ alkyl, $C_1$–$C_5$ alkoxy, $C_1$–$C_5$ alkenyloxy, $C_1$–$C_5$ alkynyloxy, cyano ($C_1C_5$) alkoxy, carboxy-($C_1$–$C_5$) alkoxy, $C_1$–$C_5$-alkoxycarbonyl($C_1$–$C_5$) alkoxy, di($C_1$–$C_5$) alkylamino, 1-imidazolyl, trifluoromethyl or cyano group; or $R_1$ is a naphthyl radical which is unsubstituted or substituted by at least one $R_5$ substituent; or $R_1$ is a pyrrole, furan, thiophene, pyrazole, imidazole, thiazole, isothiazole, oxazole, isoxazole, triazole tetrazole, thiadiazole, oxadiazole, pyrazine, N,N-dioxypyrazine, pyrimidine, N-N-dioxypyrimidine, pyridazine, pyridine, N-oxypyridine, piperidine or piperazine radical unsubstituted or substituted by at least one substituent selected from the group comprising $C_1$–$C_6$ alkyl, $C_1$–$C_6$ alkoxy, $C_1$–$C_6$ alkylthio, hydroxyl, nitro, amino, halogen or cyano, $R_2$ is $C_1$–$C_6$ alkyl, $C_1$–$C_6$ alkenyl, $C_3$–$C_7$ cycloalkyl or phenyl radical, which is unsubstituted or substituted by at least one $R_5$ substituent; $R_3$ is an $C_1$–$C_6$ alkyl, $C_1$–$C_6$ alkenyl, $C_3$–$C_7$ cycloalkyl or phenyl radical, which is unsubstituted or substituted by at least one $R_5$ substituent; or $R_3$, together with $R_2$, is a $C_3$–$C_7$ cycloalkylene radical, $R_4$ is ditetrahydropyridazinyl unsubstituted or substituted by at least one substituent selected from the group comprising $C_1$–$C_6$ alkyl, $C_1$–$C_6$ alkoxy, $C_1$–$C_6$ alkoxy-($C_1$–$C_6$) alkyl, $C_1$–$C_6$ alkylthio, hydroxy, $C_1$–$C_6$ hydroxyalkyl, amino, halogen, oxy or cyano groups, X is a valency bond, an $C_1$–$C_4$ alkylene or vinylene radical, an imino group —NH— or a carbonylamino group —CONH—; the tautomers thereof and the physiologically acceptable acid addition salts thereof with inorganic and organic acids.

2. A compound according to claim 1 wherein, wherein $R_1$ is a phenyl ring, wherein $R_5$ is a hydrogen atom, an $C_1$–$C_2$ alkylsulphonyloxy, trifluoromethylsulphonyloxy, $C_1$–$C_2$ alkylsulphenylmethyl, $C_1$–$C_2$ alkylsulphinyl-methyl, $C_1$–$C_2$ alkylsulphonylmethyl, $C_1$–$C_2$ alkylsulphonylamino, N-($C_1$–$C_2$)alkyl-($C_1$–$C_2$)alkylsulphonylamino, trifluoromethylsulphonylamino or N-($C_1$–$C_2$)alkyltrifluoromethylsulphonylamino radical, $C_1$–$C_2$ alkoxy, amino, $C_1$–$C_2$ alkylamino or di($C_1$–$C_2$)alkylamino or a sulphonyl group substituted by amino, di($C_1$–$C_2$)alkylamino or morpholino, a nitro or cyano group, a $C_1$–$C_4$ alkyl-aminosulphonyl radical, a $C_1$–$C_2$ alkylcarbonylamino, aminocarbonylamino, N-($C_1$–$C_2$-)alkylaminocarbonylamino, $C_1$–$C_2$ alkylthio, $C_1$–$C_2$ alkylsulphinyl or $C_1$–$C_2$ alkylsulphonyl radical, a halogen atom, an amino group or a hydroxy, di($C_1$–$C_3$)alkylamino, $C_1$–$C_3$ alkyl, $C_1$–$C_3$ alkoxy, $C_1$–$C_3$ alkenyloxy or $C_1$–$C_3$ alkynyloxy radical, a cyanomethoxy or methoxycarbonylmethoxy radical, a trifluoromethyl radical or a 1-imidazolyl radical; $R_6$ is a hydrogen atom, a $C_1$–$C_3$ alkyl radical, a C-$C_2$ alkoxy or di($C_1$–$C_2$)alkylamino radical or a halogen atom; and $R_7$ is a hydrogen atom or a methoxy radical; or $R_1$ is a pyrrole, furan, thiophene, pyrazole, imidazole, thiazole, isothiazole, oxazole, isoxazole, triazole, tetrazole, thiadiazole, oxadiazole, pyrazine, N,N-dioxypyrazine, pyrimidine, N,N-dioxypyrimidine, pyridazine, pyridine, N-oxypyridine, piperidine or piperazine, radical, $R_2$ is a straight-chained or branched $C_1$–$C_4$ alkyl radical, $R_3$ is a straight-chained or branched $C_1$-$C_4$ alkyl radical or, together with $R_2$, is a $C_3$-$C_6$ cycloalkylene chain, $R_4$ is a 3-oxo-2,3-dihydro-6-pyridazinyl, 5-alkyl-3-oxo2,3-dihydro-6-pyridazinyl, 3-oxo-2,3,4,5-tetrahydro-6-pyridazinyl, 5-alkyl-3-oxo-2,3,4,5-tetrahydro-6-pyridazinyl or 5-hydroxyalkyl-3-oxo-2,3,4,5-tetrahydro-6-pyridazinyl, X is a valency bond, a $C_1$-$C_2$ alkylene of vinylene radical, and imino group —NH—or a carbonylamino group —CONH—; and the tautomers thereof and the physiologically acceptable salts thereof with inorganic and organic acids.

3. A compound according to claim 1, wherein $R_1$ is a phenyl radical and $R_5$ is a hydrogen atom or a methanesulphonyloxy, trifluoromethanesulphonyloxy, methanesulphonylamino, trifluoromethanesulohonylamino, methylthio, methylsulphinyl, methylsulphonyl, hydroxyl, methyl, methoxy, propargyloxy, trifluoromethyl or 1-imidazolyl radica, $R_6$ is a hydrogen atom or a chlorine atom or a methyl, methoxy or dimethylamino radical and $R_7$ is a hydrogen atom or a methoxy radical; or $R_1$ is a pyrrole, furan, thiophene, pyrazole, imidazole, isothiazole, thiazole, oxazole, triazole, tetrazole, thiadiazole, isoxazole, oxadiazole, pyridine, N-oxypyridine, pyrazine, N,N-dioxypyrazine, pyrimidine, N,N-dioxypyrimidine, pyridazine, tetrazine, piperidine or piperazine, radical, as well as the methyl-, ethyl-, methoxy-, ethoxy-, methylthio-, ethylthio- and chlorine-substituted derivatives thereof; or $R_1$ is an indole, indazole, quinoline, isoquinoline or naphthyl radical, $R_2$ and $R_3$ are the same and are methyl radicals or $R_2$ and $R_3$ together with the carbon atom to which they are attached, form a cyclopentane or cyclohexane ring, $R_4$ is a 3-oxo-2,3,4,5-tetrahydro-6-pyridazinyl, 5-methyl-3-oxo-2,3,4,5-tetrahydro-6-pyridazinyl, 5-hydroxymethyl-3-oxo-2,3,4,5-tetrahydro-6-pyridazinyl or 3-oxo-2,3-dihydro-6-pyridazinyl and X is a valency bond, a vinylene or methylene radical, an imino group or a carbonylamino group.

4. A compound according to claim 1, wherein $R_1$ is a phenyl ring which is unsubstituted or substituted by $C_1$-$C_5$ alkyl, $C_1$-$C_5$ alkoxy, halogen or $C_1$-$C_5$ alkylthio or is a pyridyl or thienyl radical, $R_2$ and $R_3$ are the same and are methyl radicals or $R_2$ and $R_3$, together with the carbon atom to which they are attached, form a cyclopentane or cyclohexane ring, $R_4$ is a 3-oxo-2,3,4,5-tetrahydro-6-pyridazinyl, 5-methyl-3-oxo-2,3,4,5-tetrahydro-6-pyridazinyl or 3-oxo-2,3-dihydro-6-pyridazinyl radical and X is a valency bond.

5. A compound according to claim 1, which is 2,3,3-trimethyl-5-(3-oxo-2,3,4,5-tetrahydro-6-pyridazinyl)-3H-indole or a pharmaceutically acceptable salt thereof.

6. A compound according to claim 1, which is 2-(4-pyridyl)-3,3-dimethyl-5-(5-methyl-3-oxo-2,3,4,5-tetrahydro-6-pyridazinyl)-3H-indole or a pharmaceutically acceptable salt thereof.

7. A compound according to claim 1, which is 2-methylamino3,3-dimethyl-5-(3-oxo-2,3,4,5-tetrahydro-6-pyridazinyl)-3H-indole of a pharmaceutically acceptable salt thereof.

8. A pharmaceutical composition for treating heart and circulatory disease comprising an effective amount of a compound of claim 1, 2 or 3 and a pharmaceutically acceptable carrier or diluent.

9. A composition according to claim 8, wherein said composition is in the form of a tablet containing 0.5 to 500 mg of said compound.

10. A compound according to claim 1, wherein $R_1$ is a phenyl ring and $R_5$ is a hydrogen atom, an $C_1$-$C_2$ alkylsulphonyloxy, trifluoromethylsulphonyloxy, $C_1$-$C_2$ alkylsulphenylmethyl, $C_1$-$C_2$ alkylsulphinylmethyl, $C_1$-$C_2$ alkylsulphonylmethyl, $C_1$-$C_2$ alkylsulphonylamino, N-($C_1$-$C_2$)alkyl-($C_1$-$C_2$)alkylsulphonylamino, trifluoromethylsulphonylamino or N-($C_1$-$C_2$)alkyltrifluoromethylsulphonylamino radical, $C_1$-$C_2$ alkoxy, amino, $C_1$-$C_2$ alkylamino or di($C_1$-$C_2$)alkylamino or a sulphonyl group substituted by amino, di($C_1$-$C_2$)alkylamino or morpholino, a nitro or cyano group, a $C_1$-$C_4$ alkyl-aminosulphonyl radical, a $C_1$-$C_2$ alkylcarbonylamino, aminocarbonylamino, N-($C_1$-$C_2$)alkylaminocarbonylamino, $C_1$-$C_2$ alkylthio, $C_1$-$C_2$ alkylsulphinyl or $C_1$-$C_2$ alkylsulphonyl radical, a halogen atom, an amino group or a hydroxy, di($C_1$-$C_3$)alkylamino, $C_1$-$C_3$ alkyl, $C_1$-$C_3$ alkoxy, $C_1$-$C_3$ alkenyloxy or Cl-C3 alkynyloxy radical, a cyanomethoxy or methoxycarbonylmethoxy radical, a trifluoromethyl radical or a 1-imidazolyl radical.

11. A compound according to claim 1, wherein $R_1$ is a phenyl ring and $R_6$ is a hydrogen atom, a $C_1$-$C_3$ alkyl radical, a $C_1$-$C_2$ alkoxy or di($C_1$-$C_2$) alkylamino radical or a halogen atom.

12. A compound according to claim 1, wherein $R_1$ is a phenyl ring and $R_7$ is a hydrogen atom or a methoxy radical.

13. A compound according to claim 1, wherein $R_1$ is a pyrrole, furan, thiophene, pyrazole, imidazole, thiazole, isothiazole, oxazole, isoxazole, triazole, tetrazole, thiadiazole, oxadiazole, pyrazine, N,N-dioxypyrazine, pyrimidine, N,N-dioxypyrimidine, pyridazine, pyridine, N-oxypyridine, piperidine or piperazine radical.

14. A compound according to claim 1, wherein $R_2$ is a straight-chained or branched $C_1$-$C_4$ alkyl radical.

15. A Compound of claim 1, wherein $R_3$ is a straight-chained or branched $C_1$-$C_4$ alkyl radical or, together with $R_2$, is a $C_3$-$C_6$ cycloalkylene chain.

16. A compound according to claim 1, wherein $R_4$ is a 3-oxo-2,3-dihydro-6-pyridazinyl, 5-alkyl-3-oxo-2,3-dihydro-6-pyridazinyl, 3-oxo- 2,3,4,5-tetrahydro-6-pyridazinyl, 5-alkyl-3-oxo-2,3,4,5-tetrahydro-6-pyridazinyl or 5-hydroxyalkyl-3-oxo-2,3,4,5-tetrahydor-6-pyridazinyl, X is a valency bond, a $C_1$-$C_2$ alkylene or vinylene radical, an imino group—NH—or a carbonylamino group—CONH—; and the tautomers thereof and the physiologically acceptable salts thereof with inorganic and organic acids.

17. A compound according to claim 1, which is 2-(4-methoxyphenyl)-3,3-dimethyl-5-(3-oxo-2,3,4,5-tetrahydro-6-pyridazinyl)-3H-indole or a pharmacologically acceptable salt thereof.

* * * * *